United States Patent
Staib et al.

(10) Patent No.: US 8,871,068 B2
(45) Date of Patent: Oct. 28, 2014

(54) CONTINUOUS MONITOR SENSOR WITH COVALENTLY BOUND ENZYME

(75) Inventors: Arnulf Staib, Heppenheim (DE); Thomas Meier, München (DE); Reinhold Mischler, Ludwigshafen (DE); Harald Peschel, Ohlstadt (DE); Martin Hajnsek, Graz (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 724 days.

(21) Appl. No.: 12/175,578

(22) Filed: Jul. 18, 2008

(65) Prior Publication Data

US 2009/0071846 A1    Mar. 19, 2009

(30) Foreign Application Priority Data

Jul. 19, 2007   (EP) .................................... 07014218

(51) Int. Cl.
*G01N 33/487* (2006.01)
*C12Q 1/00* (2006.01)
*G01N 27/327* (2006.01)

(52) U.S. Cl.
CPC ............ *C12Q 1/001* (2013.01); *G01N 27/3272* (2013.01)
USPC ............ 204/403.01; 204/403.02; 204/403.03; 204/403.15; 205/777.5; 205/792

(58) Field of Classification Search
CPC ................. G01N 27/3272; C12Q 1/00–1/001
USPC .............. 204/403.01–403.15; 205/777.5, 792
See application file for complete search history.

(56) References Cited

U.S. PATENT DOCUMENTS

| | | |
|---|---|---|
| 4,229,536 A | 10/1980 | DeFilippi |
| 4,392,933 A | 7/1983 | Nakamura et al. |
| 4,938,860 A | 7/1990 | Wogoman |
| 5,368,707 A | 11/1994 | Henkens et al. |

(Continued)

FOREIGN PATENT DOCUMENTS

| | | |
|---|---|---|
| EP | 0247850 B1 | 4/1993 |
| EP | 0603154 B1 | 6/1994 |

(Continued)

OTHER PUBLICATIONS

Shukla, A.K., Neergat, M., Bera, P., Jayaram, V., Hegde, M.S., "An XPS study on binary and ternary alloys of transition metals with platinized carbon and its bearing upon oxygen electroreduction in direct methanol fuel cells", Journal of Electroanalytical Chemistry 504 (2001) 111-119.

(Continued)

*Primary Examiner* — Bach Dinh
(74) *Attorney, Agent, or Firm* — Roche Diagnostics Operations, Inc.

(57) ABSTRACT

The disclosure concerns a high efficiency electrochemical sensor with high signal yield for determining an analyte in a fluid medium comprising, at least one reference electrode, at least one working electrode having particles of an electrocatalyst in an electrode matrix, and an enzyme that is suitable for determining an analyte is selectively covalently bound to the particles of the electrocatalyst. The disclosure also describes a process for producing the electrochemical sensor and a method for determining an analyte in a fluid medium using the electrochemical sensor. have a high efficiency and thus achieve a high signal yield.

31 Claims, 3 Drawing Sheets

(56) References Cited

U.S. PATENT DOCUMENTS

| | | | |
|---|---|---|---|
| 5,382,346 A * | 1/1995 | Uenoyama et al. | 204/403.1 |
| 5,476,776 A | 12/1995 | Wilkins | |
| 5,593,852 A * | 1/1997 | Heller et al. | 435/14 |
| 5,998,183 A | 12/1999 | Le Fevre et al. | |
| 6,200,772 B1 | 3/2001 | Vadgama et al. | |
| 6,405,066 B1 * | 6/2002 | Essenpreis et al. | 600/347 |
| 2003/0200837 A1 * | 10/2003 | Matsuura et al. | 75/415 |
| 2004/0137547 A1 | 7/2004 | Shah et al. | |
| 2005/0189240 A1 * | 9/2005 | Lin et al. | 205/782 |
| 2005/0199494 A1 * | 9/2005 | Say et al. | 204/403.01 |
| 2007/0007133 A1 * | 1/2007 | Mang et al. | 204/403.14 |

FOREIGN PATENT DOCUMENTS

| | | | |
|---|---|---|---|
| EP | 0352925 | | 12/1994 |
| EP | 1710011 A1 | | 10/2006 |
| GB | WO2004011672 | * | 2/2004 |
| JP | 1068651 | | 3/1989 |
| WO | 99/14315 A1 | | 3/1999 |
| WO | 2004/011672 A1 | | 2/2004 |

OTHER PUBLICATIONS

CN Office Action dated Dec. 13, 2011 with English translation; issued in Chinese appl. No. 2008 10 215 431.4.

J. Wang et al., "Screen-printed amperometric biosensors for glucose and alcohols based on ruthenium-dispersed carbon inks", Analytica Chimica Acta, vol. 300, 1995, pp. 111-116.

Feldman, Ben et al., "A Continuous Glucose Sensor Based on Wired Enzyme™ Technology—Results from a 3 Day Trial in Patients with Type 1 Diabetes", Diabetes Technology & Therapeutics, vol. 5, No. 5, 2003, pp. 769-779.

Abel, Peter Ulrich et al., "Stability of immobilized enzymes as biosensors for continuous application in vitro and in vivo", Journal of Molecular Catalysis B: Enzymatic 7, (1999), pp. 93-100.

Chi, Xiaoli et al., "Amperometric biosensors based on carbon paste electrodes modified with nanostructured mixed-valence manganese oxides and glucose oxidase", Nanomedicine Nanotechnology Biology and Medicine 1, (2005), pps. pp. 130-135.

Babu, V.R. Sarath et al., "Stabilization of immobilized glucose oxidase against thermal inactivation by silanization for biosensor applications", Biosensors and Bioelectronics 19, (2004), pp. 1337-1341.

Luo, Xi-Liang et al., "A novel glucose ENFET based on the special reactivity of $MnO_2$ nanoparticles", Biosensors and Bioelectronics 19, (2004), pp. 1295-1300.

Doretti, Lucio et al., "Covalently immobilized enzymes on biocompatible polymers for amperometric sensor applications", Biosensors and Bioelectronics vol. 11, No. 4, (1996), pp. 365-373.

Leskovac, v. et al., "Glucose oxidase from *Aspergillus niger*: the mechanism of action with molecular oxygen, quinones, and one-electron acceptors", The International Journal of Biochemistry and Cell Biology 37, (2005), pp. 731-750.

Crouch, Eric et al., "A novel, disposable, screen-printed amperometric biosensor for glucose in serum fabricated using a water based carbon ink", Biosensors and Bioelectronics 21, (2005), pp. 712-718.

Luque, Guillermina L., et al., "Glucose biosensors based on the immobilization of copper oxide and glucose oxidase within a carbon paste matrix", Talanta 66 (2005), pp. 467-471.

European Search Report dated Sep. 16, 2008 for corresponding EP Application.

* cited by examiner

CONTINUOUS MONITOR SENSOR WITH COVALENTLY BOUND ENZYME

REFERENCE

This application is based on and claims priority to European Patent Application No. 07 014 218.7 filed Jul. 19, 2007, which is hereby incorporated by reference.

FIELD

The disclosure concerns an electrochemical sensor, a process for its production and a method for determining an analyte in a fluid medium using the electrochemical sensor.

BACKGROUND

Measuring systems for biochemical analysis are important components of clinically relevant analytical methods. This primarily concerns the measurement of analytes which can be directly or indirectly determined with the aid of enzymes. Biosensors, i.e., measuring systems equipped with biological components, which allow a repeated measurement of the analyte either continuously or discontinuously and which can be used ex vivo as well as in vivo have proven to be particularly suitable for the measurement of analytes. Ex vivo biosensors are typically used in flow-through cells whereas in vivo biosensors are preferably implanted into subcutaneous fat tissue. In this connection one distinguishes between transcutaneous implants which are only introduced into the tissue for a short period and are in direct contact with a measuring device located on the skin, and full implants which are inserted surgically into the tissue together with a measuring device.

Electrochemical biosensors allow the measurement of an analyte by means of two or more electrodes where at least one of the electrodes represents the working electrode on which the analyte to be determined is converted. Electrochemical biosensors which comprise an enzyme as a biological component contain the enzyme in or on the working electrode in which case for example the analyte can serve as a substrate for the enzyme and can be physicochemically altered (e.g. oxidized) by this enzyme. A redox mediator transfers the electrons released during the conversion of the analyte onto the conductive components of the working electrode, and the electrical measuring signal generated by the flow of electrons correlates with the concentration of the measured analyte.

Naturally occurring as well as synthetic redox pairs come into consideration as redox mediators. Synthetic redox mediators such as for example those described in the publication by Feldman et al. *Diabetes Technology & Therapeutics* 5 (2003), 769-779 are less suitable for in vivo applications. This is due to the fact that a synthetic redox mediator can theoretically always produce an immune response by the body when the biosensor is introduced into the body. However, at least the toxicity of these substances must be considered and, if necessary, checked because redox mediators must always be able to freely diffuse through the electrode structure by which means they can also escape from the electrode and pass over into the surrounding organism. This point is not relevant for ex vivo applications provided it is ensured that it does not enter the body due to a potential return flow of the analyte.

Consequently, electrochemical sensors which use naturally occurring redox mediators are particularly suitable for in vivo applications. The redox pair oxygen/hydrogen peroxide proves to be particularly advantageous in this connection because the initial component (oxygen) is always present. The hydrogen peroxide generated in the enzymatic conversion of an analyte by means of an oxidase in the presence of oxygen is reoxidized on the working electrode of the electrochemical biosensor whereupon an electrical signal is generated by the release of electrons and the redox mediator is converted back into its oxidized form. The kinetics of this enzymatic reaction follows a so-called ping-pong mechanism. Leskovac et al., *The International Journal of Biochemistry and Cell Biology* 37 (2005), 731-750.

Figure 1:
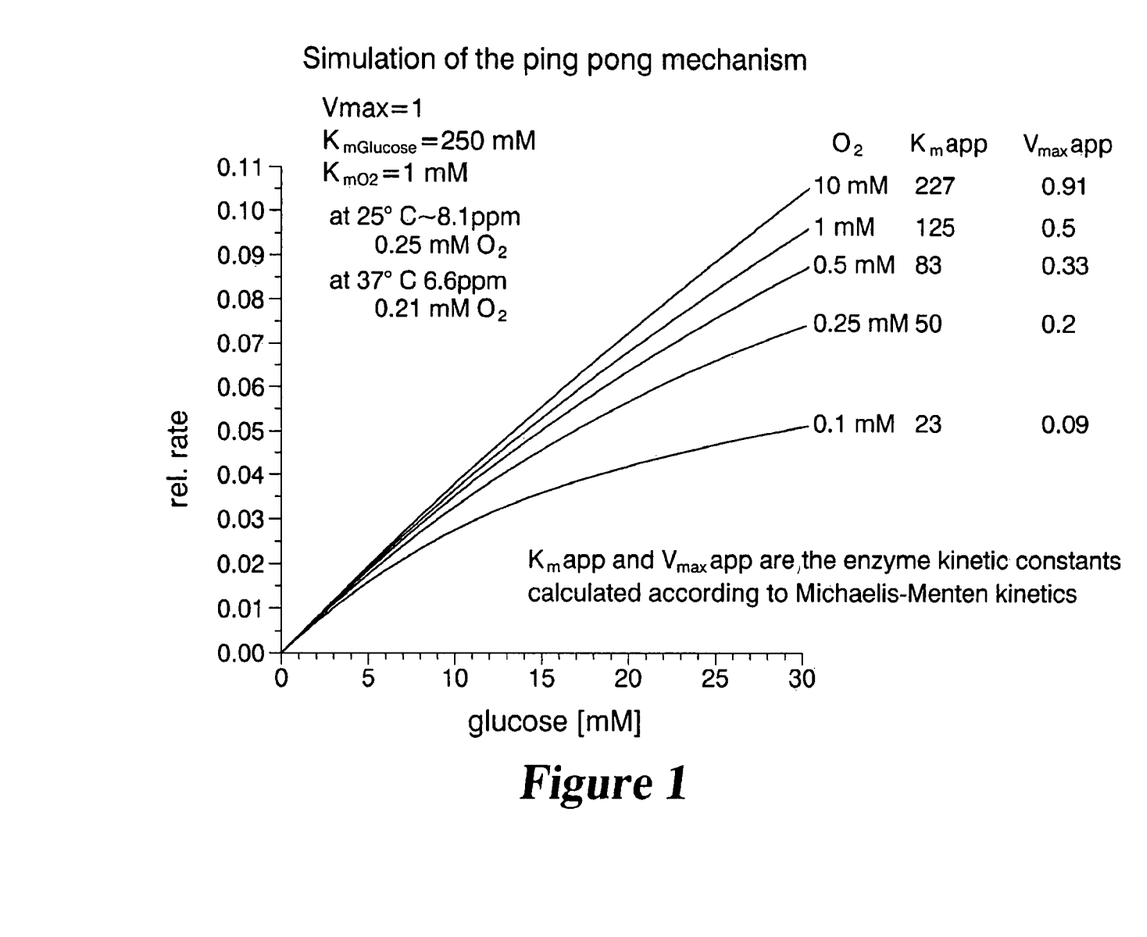
FIG. 1 shows the conversion of glucose plotted against the glucose concentration [mM] when using glucose oxidase as the enzyme and oxygen/hydrogen peroxide as the redox mediator as a function of the oxygen concentration. $K_m^{app}$ and $V_{max}^{app}$ represent the enzyme kinetic constants for glucose according to a Michaelis-Menten kinetics.

A significant problem when measuring analytes with the aid of enzymes which require oxygen as a co-substrate is, however, that temporary reductions of the oxygen concentration compared to the initial situation can occur in tissues which can affect the function of conventional in-vivo biosensors. FIG. 1 shows the kinetics of the enzymatic oxidation of glucose to glucono-δ-lactone by means of glucose oxidase at various oxygen concentrations. The graph shows that in general the amount of analyte converted at a given oxygen concentration is reduced as the glucose concentration increases and, thus, the curve is in the non-linear range in the physiologically relevant range despite the high binding constant of glucose oxidase for glucose (about 250 mM).

Furthermore, FIG. 1 shows that at higher concentrations of the analyte, an approximately linear curve is not obtained until an oxygen concentration of about 1 mM. The in vivo concentration of dissolved oxygen in aqueous systems and in particular in the interstitial fluid of subcutaneous fat tissue is, however, considerably lower. Whereas water has an approximate oxygen concentration of 0.21 mM at 37° C., the expected oxygen concentration in subcutaneous fat tissue is only 0.1 mM or even less which is why the curves are in each case curved at physiological glucose concentrations. This deviation from a linear course results in undesired transient function characteristics in in vivo biosensors.

Figure 3:
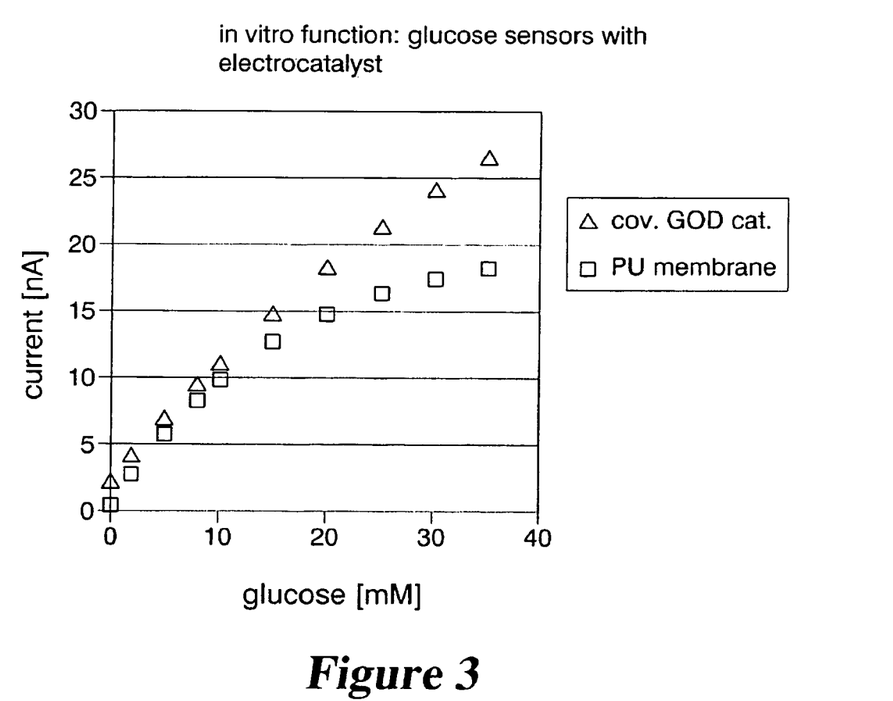
FIG. 3 shows the measuring signal [nA] of two electrochemical sensors with an immobilized enzyme plotted against the glucose concentration of a measuring solution [mM]. The measured values indicated by triangles show the function curve of an electrochemical sensor according to the present invention in which glucose oxidase was covalently bound to the electrocatalyst of the working electrode and no cover membrane was used. The measured values indicated by squares form the function curve of a sensor of identical dimensions in which the enzyme was immobilized in the working electrode by means of a cover membrane consisting of polyurethane and was not bound to the electrocatalyst by covalent binding.

Thus, the limited availability of oxygen in the tissue is a limiting factor for the linearity of the function curve of the electrochemical sensor in numerous enzymatic biosensors which require oxygen as a co-substrate. The linearity of the function curve can in principle be improved by using working electrodes with a cover membrane which inhibits the diffusion of the analyte more strongly than the diffusion of the co-substrate. FIG. 3 shows among others the function curve of an enzymatic biosensor with a cover membrane consisting of polyurethane which promotes the diffusion of oxygen more strongly than that of glucose (measured values indicated by squares). This shows that the measuring signal of the sensor can be kept approximately linear up to a glucose concentration of about 10 mM by using a suitable cover membrane. The curve becomes increasingly curved at higher concentrations.

However, the use of cover membranes in electrochemical sensors is associated with certain problems. Thus, electrochemical sensors which are used to determine different analytes must usually also contain different cover membranes in order to provide a different diffusion of the substrate and co-substrate. At the same time it must be ensured that the cover membranes are highly biocompatible for in vivo applications which involves considerable technical requirements and ultimately leads to increased production costs.

In order to lower the polarization voltage of the working electrode of an electrochemical biosensor relative to a reference electrode and thus to reduce the affect of interfering substances on the measuring signal of the working electrode, some electrochemical biosensors additionally utilize an electrocatalyst which promotes the transfer of electrons from the redox mediator onto the conductive components of the working electrode. An example of such an electrocatalyst is cobalt phthalocyanine which catalyses the oxidation of hydrogen peroxide to oxygen. Crouch et al., *Biosensors and Bioelectronics* 21 (2005), 712-718. In this process the cobalt (II) cation of the cobalt phthalocyanine complex is firstly reduced by hydrogen peroxide to cobalt (I) before it is converted back into its original divalent state with release of an electron at the anode.

Another example of an electrocatalyst known from the literature is manganese dioxide in the form of pyrolusite. Cui et al., *Nanomedicine: Nanotechnology, Biology and Medicine* 1 (2005), 130-135;.Luo et al., *Biosensors and Bioelectronics* 19 (2004), 1295-1300. Although the mechanism of the catalytic oxidation of hydrogen peroxide on manganese dioxide is not understood in detail, the potential of a working electrode with manganese dioxide as the electrocatalyst is reduced by several 100 mV compared to a working electrode without manganese dioxide. Consequently, the effect of interfering substances such as ascorbate or urea on the measuring signal is considerably reduced.

Another reason for using electrocatalysts is the damage caused to enzymes by excess hydrogen peroxide. If this substance is not sufficiently rapidly decomposed at the working electrode, a denaturation of the enzyme may occur. In order to counter this problem it was proposed in the literature to synthesize enzymes that are resistant to hydrogen peroxide, for example by mutation as shown in US 2004/0137547 A1. However, it is extremely difficult to make such modifications to an enzyme without having an adverse effect on other properties of the enzyme such as for example its enzymatic specificity. Hence, the use of electrocatalysts for conversions in which hydrogen peroxide is generated appears to be considerably superior to the above method because electrocatalysts considerably increase the efficiency of the oxidation of hydrogen peroxide and in this manner prevent excess peroxide from occurring in the electrode matrix or in its environment.

An additional problem which is associated with the formation of hydrogen peroxide in an enzymatic determination of an analyte is that hydrogen peroxide can act as an inhibitor of the analyte or of the co-substrate oxygen. This competitive inhibition depends on the concentration of hydrogen peroxide and limits the conversion of the analyte. The use of an electrocatalyst which promotes the reoxidation of hydrogen peroxide to oxygen consequently also has a positive effect with regard to the conversion of the analyte.

Various factors have to be taken into account when designing electrochemical biosensors. Thus, the biosensors have to have a sufficient amount of enzyme in the working electrode in order to prevent an enzyme limitation of the measurement. Abel et al., *Journal of Molecular Catalysis B: Enzymatic* 7 (1999), 93-100. Furthermore, the enzyme molecules should be located in the structure of the working electrode over the complete measuring period of the biosensor i.e. the enzyme should not become detached or displaced in areas of the electrode which are reached by the measuring medium. Doretti et al., *Biosensors and Bioelectronics* 11 (1996), 363-373. Finally, the enzyme should also be stable in the working electrode of the biosensor. Factors which result in a thermal deactivation of enzymes in electrochemical biosensors together with methods for their stabilization have been investigated many times. Sarath Babu et al., *Biosensors and Bioelectronics* 19 (2004), 1337-1341. Enzyme degradation after manufacture of a biosensor ultimately leads to a limited shelf-life of the sensor.

In order to take the above factors into consideration, attempts were made to stabilize the enzyme by immobilizing it in the electrode matrix of the working electrode which has led to an intensive search for suitable immobilization methods for enzymes in electrochemical biosensors. An adsorptive as well as a chemical immobilization are used in practice. However, adsorptive immobilization is disadvantageous for various reasons. On the one hand, it requires that the working electrode is covered by a membrane that is impermeable to the enzyme which increases the work required to manufacture the biosensor and makes a wide variety of demands on the membrane. On the other hand, the aforementioned displacement of enzyme molecules within the electrode cannot be prevented in the case of adsorptive immobilization which results in a change in the sensor function. U.S. Pat. No. 5,368,707 discloses biosensors which comprise working electrodes with an adsorptively bound enzyme and which are suitable for determining micromolar amounts of lead ions in liquids. In order to produce the biosensors, the surface of the working electrode consisting of a conductive material is coated with colloidal gold on the particles of which the appropriate enzyme is adsorbed which, in turn, can be covalently bound to a redox mediator Another disadvantage of electrodes provided with a cover membrane for supporting the adsorptive immobilization of enzymes which should not be underestimated especially for in vivo applications, is the necessity to non-invasively check the integrity of the cover membrane. Since even the smallest defects in the membrane are sufficient to result in a bleeding of the enzyme from the electrode into the environment, an enormous amount of checking is necessary especially in the case of in vivo biosensors. Hence, in view of the disadvantages of an adsorptive immobilization there is thus a concrete need to immobilize enzymes in electrochemical biosensors by covalent bonds to or in the electrode matrix.

Japanese Patent No. JP 10-68651 describes sensors for detecting analytes such as glucose which comprise electrodes with a covalently bound enzyme. For this purpose, the surface of the electrodes coated with $SnO_2$ as a conductive material is activated with a strong acid, functionalized with a coupling reagent and finally brought into contact with the enzyme.

European Patent No. EP 0 247 850 A1 discloses biosensors for the amperometric detection of an analyte. These sensors contain electrodes with immobilized enzymes which are immobilized or adsorbed onto the surface of an electrically conducting support where the support consists of a platinized porous layer of resin-bound carbon or graphite particles or contains such a layer. For this purpose, electrodes made of platinized graphite and a polymeric binding agent are firstly prepared and these are subsequently brought into contact with the enzyme. In this case, the enzyme is immobilized either by adsorption to the electrode surface or by coupling it to the polymeric binding agent using suitable reagents.

Amperometric biosensors with electrodes comprising an enzyme immobilized or adsorbed onto or into an electrically conducting, porous electrode material are also described in EP 0 603 154 A2. In order to produce the enzyme electrodes, an oxide or oxide hydrate of a transition metal of the fourth period, such as for example manganese dioxide, acting as a catalyst is worked into a paste together with graphite and a non-conducting polymeric binding agent, and the porous electrode material obtained after drying the paste is brought into contact with the enzyme in a second step. The enzyme can be immobilized on or in the porous electrode material by cross-linking using glutardialdehyde.

A major disadvantage of the electrochemical biosensors described in JP 10-68651, EP 0 247 850 A1 and EP 0 603 154 A2 is that the enzyme is first immobilized on the electrode that has been prefabricated without enzyme. As a consequence, there is the problem that the enzyme cannot be coupled to the electrode components in a controlled manner. Thus, when glutardialdehyde is used as a cross-linking reagent, the enzyme not only binds in an uncontrolled manner to any reactive components of the electrode material, but is also inter-crosslinked. Furthermore, this procedure contaminates the electrode with the reagents that are used and, hence, the electrode has to again be thoroughly cleaned especially before use in an in vivo biosensor which increases the production complexity and thus the costs.

U.S. Pat. No. 4,938,860 discloses a suitable electrode for electrochemical sensors comprising a platinum coated anode formed as a film and an enzyme layer which is bound to the anode. The enzyme layer is bound to the platinized anode preferably by using an aminosilane and a suitable cross-linking agent such as for example glutardialdehyde. However, a disadvantage of the electrode described in U.S. Pat. No. 4,938,860 is that due to the construction of the anode as a film only a small surface is provided for the enzymatic conversion of the analyte and platinum is a relatively expensive material to use as a catalyst.

SUMMARY

Hence, embodiments of the invention provide an enzymatic electrochemical sensor for determining an analyte in which the disadvantages of the prior art are at least partially eliminated. In particular, the sensor should ensure a specific and durable immobilization of the enzyme, have a high efficiency and thus achieve a high signal yield. Furthermore, it should be possible to produce the sensor in. a simple and low-cost manner.

Embodiments of the electrochemical biosensor for determining an analyte in a fluid medium, comprises at least one working electrode and at least one reference electrode, wherein at least the working electrode comprises particles of an electrocatalyst in an electrode matrix and wherein an enzyme that is suitable for determining the analyte is covalently bound to the particles of the electrocatalyst.

In a further aspect, the present disclosure concerns a process for producing an electrochemical sensor according to the invention, comprising the following steps: (a) providing electrocatalyst particles; (b) coating the electrocatalyst particles with an enzyme, wherein the enzyme is covalently bound to the electrocatalyst particles; (c) mixing the electrocatalyst particles coated covalently with enzyme that are obtained in step (b) with a conductive electrode material and optionally further substances; (d) processing the mixture obtained in step (c) to form an electrode; arid, (e) combining the electrode obtained in step (d) with at least one further electrode.

The production process according to embodiments of the invention does in fact prove to be particularly advantageous because the production of the electrocatalyst coated with enzyme can be carried out separately from the production of the electrode. Furthermore, the electrocatalyst covalently coated with enzyme provides a defined starting material for the preparation of the electrode paste, which starting material can be purified before introduction into the electrode paste thus obviating a subsequent cleaning of the finished electrode.

In yet a further aspect, embodiments of the present invention concerns a method for determining an analyte in a fluid medium, comprising the following steps. (a) contacting the fluid medium with an electrochemical sensor according to the invention; and, (b) determining the presence or/and the amount of analyte in the fluid medium by measuring a signal generated by the electrochemical sensor.

BRIEF DESCRIPTION OF THE DRAWINGS

Embodiments of the invention are further elucidate by the following figures.

DETAILED DESCRIPTION

Embodiments of the electrochemical biosensor for determining an analyte in a fluid medium, comprises at least one working electrode and at least one reference electrode, wherein at least the working electrode comprises particles of an electrocatalyst in an electrode matrix and wherein an enzyme that is suitable for determining the analyte is covalently bound to the particles of the electrocatalyst.

A metal oxide can be used as the electrocatalyst which is present in the electrode matrix of at least the working electrode. The metal oxide can be any metal oxide which is able to catalyse the conversion of a redox mediator used to determine the analyte. In other embodiments the electrocatalyst that is used is a metal oxide selected from the group consisting of $MnO_2$, $FeOOH$, $Fe_3O_4$, $Fe_2O_3$, $Cr_2O_3$ and $V_2O_5$, with $MnO_2$ being particularly suitable. Furthermore, it is desirable that the electrocatalyst has a high affinity for oxygen.

The electrocatalyst is provided according to embodiments of the invention in a particulate form, wherein the particle size can be varied depending on the respective requirements. Within the scope of the invention embodiments, 90% of the electrocatalyst particles usually have a diameter of 0.1 μm to 20 μm, a diameter of 0.5 μm to 5 μm having proven to be particularly preferred. In any case, the particle size of the electrocatalyst should always be less than the layer thickness of the working electrode which is in the range of 1 μm to 50 μm, preferably in the range of 5 μm to 20 μm.

The ability to control the effective surface of the electrocatalyst by means of the particle size is of crucial importance especially for its functionalization with enzyme. Thus, a higher effective surface of the electrocatalyst can also increase its loading with enzyme and thus result in a higher enzyme activity stated in units per milligram electrocatalyst which in general is determined by the amount of electrocatalyst in the working electrode as well as its porosity and area. The term "unit" as used within the scope of the present application represents the amount of enzyme which is required to convert 1 μmol substrate per minute under standard conditions. The enzyme-coated electrocatalyst particles used for the purposes of the present invention usually have an enzyme activity of about 0.01 U/mg to about 10 U/mg, with an enzyme activity of about 0.1 U/mg to about 10 U/mg having proven to be particularly advantageous.

In the electrochemical sensor according to embodiments of the invention the enzyme is selectively covalently bound to the particles of the electrocatalyst, with the enzyme particularly preferably having no covalent bonds with the other components of the electrode matrix. The covalent binding of the enzyme to the electrocatalyst has the advantage that the diffusion path of the redox mediator to catalytically active sites of the electrode can be kept small which results in a high efficiency of the working electrode and thus a high signal yield of the electrochemical sensor.

Furthermore, after regeneration by the electrocatalyst, the redox mediator is also adsorptively bound to the electrocatalyst as a result of which, for example in the case of an oxygen/hydrogen peroxide system, a local high oxygen activity is generated in the region of the surface of the electrocatalyst which decreases towards the surrounding measuring medium. On the other hand, the covalent binding of the enzyme to the electrocatalyst results in a high local activity of regenerated redox mediator on the enzyme, which is reflected by a higher linearity and stability of the generated measuring signal in relation to the concentration of analyte as shown for example in FIG. 3 (measured values shown as triangles). In this case, even a transient lowering of the concentration of the redox mediator in the environment for example due to an impaired blood circulation of the tissue, does not lead to a transient change of the measuring signal.

Finally, the covalent coupling of the enzyme to the electrocatalyst ensures the constancy of the function because a detachment of enzyme molecules can be ruled out under the typical measurement conditions (physiological electrolyte concentration, physiological pH, body temperature). Thus, the electrochemical sensor according to embodiments of the invention remains operational over a long time period and virtually operates free of drift. In order to covalently bind the enzyme to the particles of the electrocatalyst, the disclosed electrocatalyst particles have a functionalized surface and in particular a surface functionalized with amino groups or/and carboxyl groups to which the enzyme is bound. The surface can for example be functionalized by coating the electrocatalyst particles with a suitable reagent to form functional groups on the surface of the electrocatalyst particles by means of which the enzyme can be covalently bound to the electrocatalyst particles.

Coating reagents which are used within the scope of the disclosure are substances which, on the one hand, undergo a covalent binding with the electrocatalyst e.g. with hydroxy groups of the electrocatalyst and, on the other hand, contain at least one functional group which serves to covalently bind the enzyme. This means that the coating reagents are at least bifunctional i.e. comprise at least two functional groups. The functional groups of the coating reagent which are used for covalent binding to the electrocatalyst and for covalent binding to the enzyme can be the same or different but are preferably different. Coating reagents can be silanes which carry at least one suitable functional group by means of which the enzyme is covalently bound to the coating reagent.

The surface of the electrocatalyst particles can be functionalized with an aminosilane which binds to the surface of the electrocatalyst particles while forming silicon-oxygen bonds and at the same time provides free amino groups for a covalent binding of the enzyme to the electrocatalyst particles. Suitable aminosilanes comprise for example 3-aminopropyltrimethoxysilane and 3-amino-propyltriethoxysilane.

Alternatively, the surface of the electrocatalyst particles can be functionalized with a carboxysilane which binds to the surface of the electrocatalyst particles while forming silicon-oxygen bonds and, optionally after hydrolysis, provides free carboxyl groups for a covalent binding of the enzyme to the electrocatalyst particles. In this connection, 3-(triethoxysilyl)-propyl succinic acid anhydride which is commercially available as Geniosil® GF 20 (Wacker Company) has proven to be a particularly suitable silane.

The enzyme can be covalently bound to the functionalized surface of the electrocatalyst particles either directly or by means of cross-linking reagents. In some embodiments, the enzyme is directly bound to the functionalized surface of the electrocatalyst particles. The enzyme can be coupled to the functionalized surface of the electrocatalyst particles in any manner and can comprise a prior activation of functional groups on the functionalized surface of the electrocatalyst particles or/and of the enzyme. Functional groups can for example be activated by reacting the functionalized electrocatalyst or/and the enzyme with a suitable activation reagent. Preferred activation reagents comprise carbodiimides such as for example dicyclohexylcarbodiimide (DCC), diisopropylcarbodiimide or 1-ethyl-3-(3-dimethylaminopropyl)carbodiimide (EDC) as well as combinations of carbodiimides and succinimides. A particularly suitable activation reagent for the purposes of embodiments of the present invention comprises a combination of 1-ethyl-3-(3-dimethylaminopropyl)-carbodiimide (EDC) and N-hydroxysuccinimide.

In another embodiment, the enzyme is bound to the functionalized surface of the electrocatalyst particles by a cross-linking reagent, with the cross-linking reagent having reactive groups which can react covalently with the functional groups on the functionalized surface of the electrocatalyst particles as well as with the functional groups of the enzyme. Particularly preferably reactive groups are present which enable a cross-linking between the enzyme and the functional groups on the surface of the electrocatalyst particles. Any reagents which can fulfil the function described above come into consideration as cross-linking reagents such as for example polyfunctional aldehydes and in particular dialdehydes such as glutardialdehyde, benzoquinones, bromocyanogen, hydrazines, succinimides, 2,4,6-trichloro-1,3,5-triazine or combinations thereof. A succinimide, more preferably a disuccinimide and most preferably disuccinimidyl suberate (DSS) is preferably used as a cross-linking reagent.

The electrode matrix of the working electrode can be generated by mixing the electrocatalyst particles covalently coated with enzyme with other components of the electrode matrix e.g. with a conductive electrode material and subsequently drying the mixture that is obtained, with the electrode matrix usually containing the electrocatalyst in an amount of about 1% by weight to about 50% by weight, preferably in an amount of about 5% by weight to about 20% by weight.

In another embodiment, the electrode matrix is in a porous form. The porosity of the electrode matrix can among others be regulated by the particle size of the electrocatalyst and other components, where a high porosity is associated with a larger effective surface of the electrode and thus a larger area of contact to the measuring medium. The conductive electrode material which can for example be provided in the form of a paste to produce the electrode matrix preferably comprises conductive solid particles such as graphite or/and fullerene in combination with a non-conducting binding agent, and in particular with a non-conducting polymeric binding agent such as for example a perfluorinated polymer such as Nafion.

The enzyme immobilized on the electrocatalyst particles can be an oxidase and in particular alcohol oxidase (1.1.3.13), arylalcohol oxidase (EC 1.1.3.7), catechol oxidase (EC 1.1.3.14), cholesterol oxidase (EC 1.1.3.6), choline oxidase (I.1.3.17), galactose oxidase (EC 1.1.3.9), glucose oxidase (EC 1.1.3.4), glycerol-3-phosphate oxidase (EC 1.1.3.21), hexose oxidase (EC 1.1.3.5), malate oxidase (EC 1.1.3.3), pyranose oxidase (EC 1.1.3.10), pyridoxine-4-oxidase (EC 1.1.3.12) or thiamine oxidase (EC 1.1.3.23). The enzyme is particularly preferably glucose oxidase.

The reference electrode of the electrochemical sensor according to the disclosure serves to adjust the polarization potential of the working electrode and can consist of any material which is suitable for the purposes of the present invention. A silver/silver chloride electrode can be used as the reference electrode.

Furthermore, the electrochemical sensor of the disclosure can, in addition to the at least one working electrode and the at least one reference electrode, comprise at least one counter electrode which is in the form of a noble metal electrode and in particular a gold electrode. A counter electrode in the form of a noble metal electrode is preferably coated with a suitable conductive material such as for example a paste containing conductive solid particles, in particular carbon paste.

According to the disclosure, the electrochemical sensor can contain two sections. The first section which can be brought into contact with the fluid medium containing the analyte comprises the electrodes i.e. working electrode, reference electrode and optionally counter electrode. This section is preferably provided with a biocompatible coating. The biocompatible coating allows the analyte to penetrate into the electrode matrix but should prevent electrode components from escaping into the surrounding medium. In view of the fact that due to the covalent binding of the enzyme to the electrocatalyst the enzyme does not bleed out of the working electrode or the electrochemical sensor, a biocompatible coating is not absolutely necessary for many applications. Thus, the electrochemical sensor according to the disclosure can also be used especially in in vivo biosensors when the biocompatible coating is not a barrier to enzymes. On the contrary, a biocompatible coating can be selected in this connection which provides an optimal interaction with the surrounding tissue or/and blood or serum.

Biocompatible coatings can be generated in various ways. A preferred method is to use prefabricated membranes which are applied to the electrochemical sensor. The membrane can be immobilized on the sensor by various techniques, with gluing or laser welding being regarded as preferred. Prefabricated dialysis membranes have proven to be advantageous in this connection, and dialysis membranes made of polyether sulfone such as those disclosed for example in EP 1 710 011 A1 which are commercially available under the trade name Ultrason® 6020 (BASF Company) are particularly suitable.

Alternatively, the biocompatible coating can be generated in situ by applying a solution of a suitable polymer onto the electrochemical sensor and subsequently drying it. The application of the polymer onto the biosensor is preferably carried out by spraying, dip-coating or dispersing a dilute solution of the polymer but is not limited to these methods. An organic solvent is preferably used as the solvent and in particular an organic solvent with a boiling point of ≤100° C. such as for example ethanol, the solvent containing an amount of about 0.1% by weight to about 30% by weight, preferably of about 0.5% by weight to about 15% by weight polymer. Polymers which are suitable for such purposes comprise in particular polymers having a zwitterionic structure and mimicing cell surfaces such as for example 2-methacryloyloxyethyl-phosphorylcholine-co-n-butyl-methacrylate (MPC-co-BMA). The biocompatible coatings that are obtained usually have a thickness of about 1 µm to about 100 µm, preferably of about 3 µm to about 25 µm.

The second section of the electrochemical sensor lies in a region that is inaccessible to the fluid measuring medium and preferably comprises a unit for registering measured values. In a further embodiment, the second section additionally comprises a voltage source such as for example a battery or an accumulator and a unit which is selected from a wireless data transfer unit and a display for displaying the measured values. Alternatively, the second section can comprise an interface for a measured value registration unit that is separate from the electrochemical sensor.

The electrochemical sensor according to the disclosure can be designed for multiple measurements i.e. the sensor enables a repeat measurement of the analyte to be determined. This is particularly desirable in applications in which a constant i.e. continuous or discontinuous control of the presence or/and the amount of an analyte is to take place over a longer time period of e.g. one day or longer, in particular one week or longer such as for example in the case of dialysis patients. In one embodiment, the invention consequently provides that the electrochemical sensor is designed as a flow-through cell through which a fluid containing the analyte is passed. Alternatively, the electrochemical sensor according to the disclosure can, however, also be designed as a fully or partially implantable device which for example can be implanted into fat tissue or into blood vessels.

The electrochemical sensor according to the disclosure can be used to determine an analyte in a fluid medium which can originate from any source. In one embodiment, the electrochemical sensor is used to determine an analyte in a body fluid comprising but not limited to whole blood, plasma, serum, lymph fluid, bile fluid, cerebrospinal fluid, extracellular tissue fluid, urine as well as glandular secretions such as saliva or sweat, wherein whole blood, plasma, serum and extracellular tissue fluid are regarded as particularly suitable. The amount of sample required to carry out the analysis is usually from about 0.01 µl to about 100 µl, preferably from about 0.1 µl to about 2 µl.

The analyte to be determined qualitatively or/and quantitatively can be any biological or chemical substance which can be detected by means of a redox reaction. The analyte is preferably selected from the group consisting of malic acid, alcohol, ammonium, ascorbic acid, cholesterol, cysteine, glucose, glutathione, glycerol, urea, 3-hydroxybutyrate, lactic acid, 5'-nucleotidase, peptides, pyruvate, salicylate and triglycerides. In one embodiment, the analyte to be determined by means of the electrochemical sensor according to the invention is glucose.

In a further aspect, the present disclosure concerns a process for producing an electrochemical sensor according to the invention, comprising the following steps: (a) providing electrocatalyst particles; (b) coating the electrocatalyst particles with an enzyme, wherein the enzyme is covalently bound to the electrocatalyst particles; (c) mixing the electrocatalyst particles coated covalently with enzyme that are obtained in step (b) with a conductive electrode material and optionally further substances; (d) processing the mixture obtained in step (c) to form an electrode; and, (e) combining the electrode obtained in step (d) with at least one further electrode.

The production process according to the invention does in fact prove to be particularly advantageous because the production of the electrocatalyst coated with enzyme can be carried out separately from the production of the electrode. Furthermore, the electrocatalyst covalently coated with enzyme provides a defined starting material for the preparation of the electrode paste, which starting material can be purified before introduction into the electrode paste thus obviating a subsequent cleaning of the finished electrode.

In order to produce the electrochemical sensors according to the invention, particles of an electrocatalyst as defined above, are preferably firstly reacted with a coating reagent by means of which the surface of the electrocatalyst particles is functionalized. By successively reacting the functionalized electrocatalyst particles with a cross-linking reagent and an enzyme, electrocatalyst particles covalently coated with enzyme are obtained which can be processed to form an electrode matrix by mixing them with other components as defined above.

In order to determine the analyte, the electrochemical sensor can be designed in any manner which allows a contact between the electrochemical sensor and the fluid medium. Thus, the sensor can for example be designed as a flow-through cell through which the medium containing the analyte flows. On the other hand, the sensor can also be designed as a diffusion sensor, wherein the contact between the sensor and medium takes place by diffusion. Equally, the electrochemical sensor can be designed as a device which is intended to be completely or partially implanted into the body of a patient, in which case it is implanted either into a blood vessel or into tissue and in particular into subcutaneous fat tissue.

In yet a further aspect, the present invention concerns a method for determining an analyte in a fluid medium, comprising the following steps. (a) contacting the fluid medium with an electrochemical sensor according to the invention; and, (b) determining the presence or/and the amount of analyte in the fluid medium by measuring a signal generated by the electrochemical sensor.

A measurable signal is generated by the sensor depending on the presence or/and the amount of analyte. This signal is preferably an electrical signal such as for example electrical current, voltage, resistance etc. which is evaluated or read-out using suitable means. The electrochemical sensor can be an amperometric sensor.

Embodiments of the invention are further elucidate by the following examples.

Example 1

Preparation of carboxy-functionalized manganese dioxide. 1.6 g manganese dioxide (Technipur Company) was suspended in 256 ml toluene, 84 g Geniosil® GF 20 (Wacker Company) was added to the resulting suspension and the reaction mixture was stirred for 24 hours at 50° C. and 520 rpm under a nitrogen atmosphere in order to prepare carboxy-functionalized manganese dioxide. After cooling and sedimentation of the manganese dioxide, the toluene was decanted and the residue was washed twice with 250 ml toluene each time as well as subsequently once with 250 ml acetone. 250 ml water was added to the functionalized manganese dioxide obtained in this manner and stirred for 24 h at room temperature. Subsequently, the water was centrifuged and the residue was dried under a vacuum at 50° C. over CaCl2 to obtain about 1.5 mg of carboxy-functionalized manganese dioxide.

Example 2

Coupling of glucose oxidase to carboxy-functionalized manganese dioxide. 500 mg 1-ethyl-3-(3-dimethylaminopropyl)carbodiimide (EDC), 400 mg N-hydroxysuccinimide and 70 mg glucose oxidase was added to 100 mg of the dried, carboxy-functionalized manganese dioxide from example 1 and stirred for 24 h at room temperature in an aqueous solution. After the solid had sedimented, the supernatant was removed and the solid was washed four times with potassium phosphate buffer pH 7.4. After drying the solid obtained in air, about 85 mg of enzyme-coated electrocatalyst was obtained which had an enzyme activity of 0.06 U/mg.

Example 3

Preparation of amino-functionalized manganese dioxide. 8 ml 3-aminopropyltriethoxysilane (Sigma Company) was added to a well-stirred suspension of 200 mg manganese dioxide (Technipur Company) in 32 ml toluene that had been heated to 60° C. and the mixture was stirred for a further 16 h at 60° C. After sedimentation of the solid, the clear supernatant was decanted and the solid was washed three times with 32 ml toluene each time. The remaining solid was dried in air to obtain about 182 mg of amino-functionalized manganese dioxide.

Example 4

Coupling of glucose oxidase to amino-functionalized manganese dioxide using glutardialdehyde as the cross-linking reagent. The dried solid from example 3 was washed once with 32 ml 50 mM potassium phosphate buffer pH 7.4 and subsequently taken up in 16 ml 50mM potassium phosphate buffer pH 7.4. 16 ml of a 10% glutardialdehyde solution (Sigma Company) was added to this suspension while stirring. The reaction was terminated after 1.5 h at 25° C. The sedimented solid was washed three times with 32 ml 50 mM potassium phosphate buffer pH 7.4 each time, suspended in 16 ml of the same buffer while stirring and admixed with 16 ml of a solution of 0.5 mg/ml glucose oxidase (Roche Company) in 50 mM potassium phosphate buffer pH 7.4. This mixture was stirred for 3 h at 25° C. After the solid had sedimented, it was washed four times with 16 ml 50 mM potassium phosphate buffer pH 7.4 each time. After lyophilisation, about 200 mg of enzyme-coated electrocatalyst was obtained which had an enzyme activity of 0.12 U/mg.

Example 5

Coupling of glucose oxidase to amino-functionalized manganese dioxide using disuccinimidyl suberate as the cross-linking reagent. 0.02 mg disuccinimidyl suberate in 20 µl dioxane and 0.008 mg glucose oxidase in 2 ml 0.1 M potassium phosphate buffer pH 8.5 were added to 20 mg of the dried, amino-functionalized manganese dioxide from example 3 and stirred for 4 h at room temperature. After centrifuging the solid, it was washed twice with 5 ml 0.1 M potassium phosphate buffer pH 8.5 each time and subsequently taken up in 5 ml 0.1 M potassium phosphate buffer pH 8.5. After lyophilization, about 18.8 mg of the enzyme-coated electrocatalyst was obtained which had an enzyme activity of 0.1 U/mg.

Example 6

Preparation of amperometric sensors. In order to prepare an electrochemical sensor with three electrodes (working electrode, reference electrode and counter electrode) which allows the determination of glucose in blood or subcutaneous fat tissue, a working electrode without a cover membrane was prepared in the first step. For this purpose, manganese dioxide functionalized with glucose oxidase according to example 5 was mixed with carbon polymer paste PE 401 (Acheson Company) and diethylene glycol monobutyl ether, and the mixture obtained was applied by means of a dispensing technique onto the gold surface of a sensor strip made of polyester and dried at 25° C. in a vacuum. The working electrode obtained in this manner was combined with a silver/silver chloride electrode as the reference electrode and with a gold electrode as the counter electrode. The conducting paths were insulated.

Example 7

Figure 2:
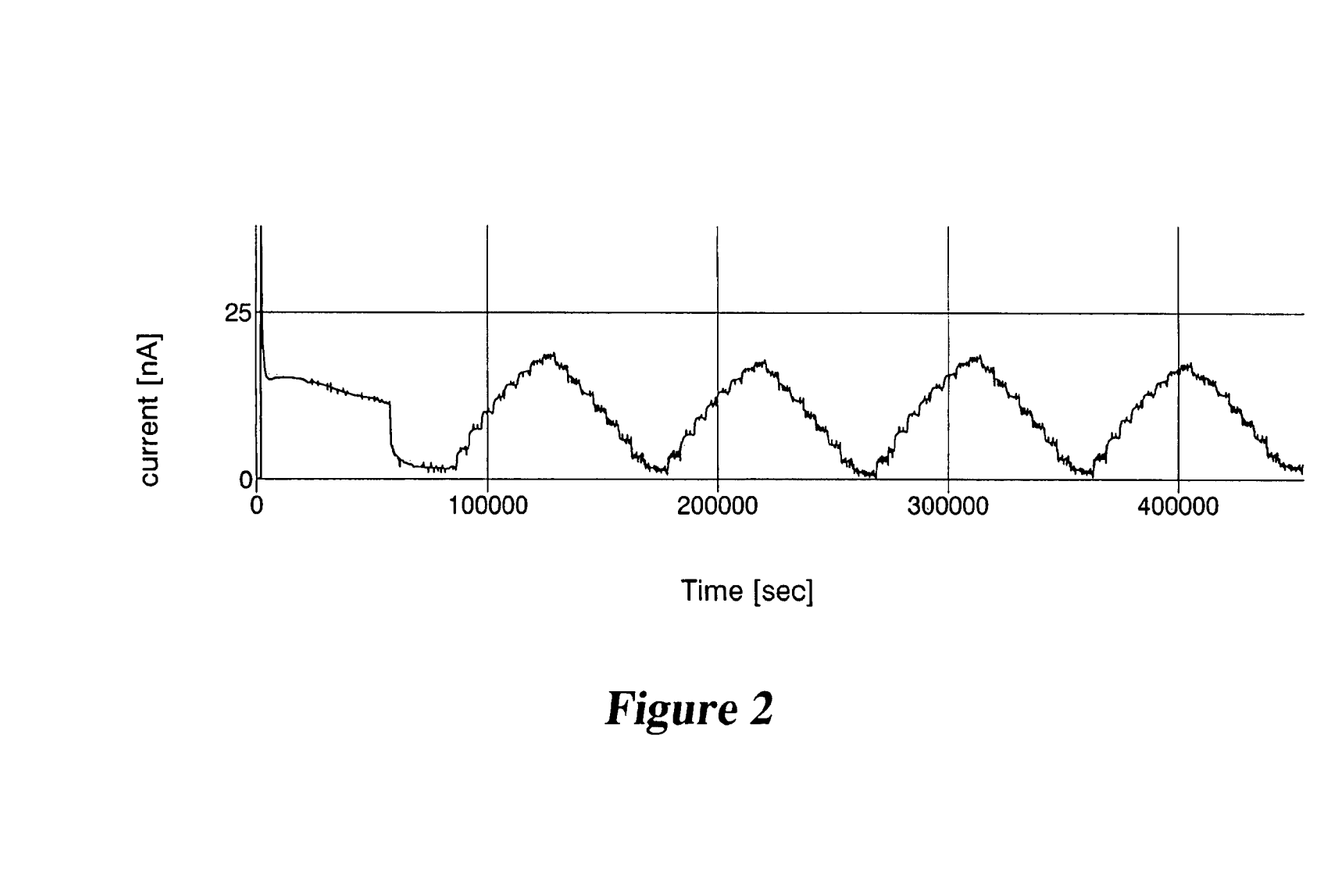
FIG. 2 shows the measured signal [nA] of an electrochemical sensor according to the present invention plotted against time [sec] in the course of a 7 day measurement of the glucose concentration of a measuring solution in which the glucose concentration was periodically varied between 0 and 26 mM. An electrode without a cover membrane was used as the working electrode which contained manganese dioxide coated with glucose oxidase as the electrocatalyst and was prepared according to Example 6 of the present application.

Determining the stability and linearity of the measured signal of amperometric sensors. The electrochemical sensor obtained according to example 6 was immersed in a glucose solution located in a flow-through chamber and measured for 7 days during which the concentration of the glucose solution was continuously varied between 0 and 26 mM. FIGS. 2 and 3 show the results of this measurement.

Thus, embodiments of the high efficiency and high yield continuous monitor sensor with covalently bound enzyme are disclosed. One skilled in the art will appreciate that the teachings can be practiced with embodiments other than those disclosed. The disclosed embodiments are presented for purposes of illustration and not limitation, and the invention is only limited by the claims that follow.

What is claimed is:

1. An electrochemical sensor for determining an analyte in a fluid medium, comprising:
    at least one reference electrode;
    at least one working electrode comprising:
        particles of an electrocatalyst in an electrode matrix, and
        an enzyme that is suitable for determining an analyte is selectively covalently bound to the particles of the electrocatalyst wherein the enzyme has no covalent bonds with other components of the electrode matrix;
    wherein the electrode matrix is in a porous form and the electrode matrix additionally contains a conductive electrode material.

2. The electrochemical sensor in claim 1 wherein the electrocatalyst is a metal oxide, in particular a metal oxide selected from the group consisting of $MnO_2$, $FeOOH$, $Fe_3O_4$, $Fe_2O_3$, $Cr_2O_3$ and $V_2O_5$.

3. The electrochemical sensor in claim 1 wherein the electrocatalyst is $MnO_2$.

4. The electrochemical sensor in claim 1 wherein 90% of the electrocatalyst particles have a diameter of about 0.1 µm to about 20 µm.

5. The electrochemical sensor in claim 1 wherein the enzyme that is selectively covalently bound to the particles of the electrocatalyst has an enzyme activity of about 0.01 U/mg to about 10 U/mg.

6. The electrochemical sensor in claim 1 wherein the electrode matrix contains the electrocatalyst in an amount of about 1% by weight to about 50% by weight.

7. The electrochemical sensor in claim 1 wherein the electrochemical sensor is designed for multiple measurements.

8. The electrochemical sensor in claim 1 wherein the electrochemical sensor is designed as a fully or partially implantable device.

9. The electrochemical sensor in claim 1 wherein the electrochemical sensor is designed as a flow-through cell.

10. The electrochemical sensor in claim 1 wherein the electrochemical sensor is designed for determining an analyte in a body fluid, in particular in whole blood.

11. The electrochemical sensor in claim 1 wherein the electrochemical sensor is designed for determining an analyte selected from the group consisting of malic acid, alcohol, ammonium, ascorbic acid, cholesterol, cysteine, glucose, glutathione, glycerol, urea, 3-hydroxybutyrate, lactic acid, 5'-nucleotidase, peptides, pyruvate, salicylate and triglycerides.

12. The electrochemical sensor in claim 1 wherein the electrocatalyst particles have a functionalized surface to which the enzyme is bound.

13. The electrochemical sensor in claim 12 wherein the surface of the electrocatalyst particles is functionalized with amino groups or carboxyl groups.

14. The electrochemical sensor in claim 12 wherein the surface of the electrocatalyst particles is functionalized with an aminosilane and in particular with 3-aminopropyltriethoxysilane.

15. The electrochemical sensor in claim 12 wherein the surface of the electrocatalyst particles is functionalized with a carboxy-silane and in particular with 3-(triethoxysilyl)propyl succinic acid anhydride.

16. The electrochemical sensor in claim 12 wherein the enzyme is directly bound to the functionalized surface of the electrocatalyst particles.

17. The electrochemical sensor in claim 12 wherein the enzyme is bound to the functionalized surface of the electrocatalyst particles by means of a cross-linking reagent.

18. The electrochemical sensor in claim 17 wherein the cross-linking reagent is a succinimide and in particular disuccinimidyl suberate.

19. The electrochemical sensor in claim 1 wherein the enzyme is an oxidase.

20. The electrochemical sensor in claim 19 wherein the enzyme is glucose oxidase.

21. The electrochemical sensor in claim 1 further comprising a counter electrode.

22. The electrochemical sensor in claim 21 wherein the counter electrode is coated with a conductive material.

23. The electrochemical sensor in claim 1 wherein the electrochemical sensor contains at least two sections, wherein the first section comprises the electrodes, is provided with a biocompatible coating and can be brought into contact with the fluid medium containing the analyte and wherein the second section is in an area that is inaccessible to the fluid medium.

24. The electrochemical sensor in claim 23 wherein the biocompatible coating is formed by applying a prefabricated membrane onto the sensor.

25. The electrochemical sensor in claim 23 wherein the biocompatible coating is formed by applying a solution of a polymer to the sensor and subsequent drying.

26. The electrochemical sensor in claim 25 wherein the polymer is 2-methacryloyloxyethyl-phosphorylcholine-co-n-butyl-methacrylate.

27. The electrochemical sensor in claim 23 wherein the biocompatible coating has a thickness of about 1 µm to about 100 µm.

28. The electrochemical sensor in claim 23 wherein the second section comprises a unit for registering measured values.

29. The electrochemical sensor in claim 23 wherein the second section additionally comprises a voltage source and an element selected from a wireless data transfer unit and a display for displaying measured values.

30. The electrochemical sensor in claim 23 wherein the second section comprises an interface for a unit for registering measured values that is separate from the electrochemical sensor.

31. A method for determining an analyte in a fluid medium, comprising the steps of:
(a) contacting the fluid medium with a reference electrode;
(b) contacting the fluid medium with a working electrode comprising:
particles of an electrocatalyst in an electrode matrix, and
an enzyme that is suitable for determining an analyte is selectively covalently bound to the particles of the electrocatalyst wherein the enzyme has no covalent bonds with other components of the electrode matrix; and
(c) determining the presence or/and the amount of the analyte in the fluid medium by measuring a signal generated by the electrochemical sensor;
wherein the electrode matrix is in a porous form and the electrode matrix additionally contains a conductive electrode material.

\* \* \* \* \*